United States Patent
Ralph et al.

(10) Patent No.: US 11,883,003 B2
(45) Date of Patent: Jan. 30, 2024

(54) COMPLIANT, ATRAUMATIC SHEATH TIPS

(71) Applicant: GYRUS ACMI, INC. D.B.A. OLYMPUS SURGICAL TECHNOLOGIES AMERICA, Westborough, MA (US)

(72) Inventors: Christopher R. Ralph, Woodinville, WA (US); Jean-Martin Baillargeon, Seattle, WA (US); Jason T. Panzenbeck, Seattle, WA (US); Taylor N. Tyson, Seattle, WA (US); Nathan J. Dale, Mill Creek, WA (US); Sujeeth Parthiban, Redmond, WA (US); Anthony H. Siuda, Redmond, WA (US)

(73) Assignee: Gyrus ACMI, Inc. d/b/a Olympus Surgical Technologies America, Westborough, MA (US)

( * ) Notice: Subject to any disclaimer, the term of this patent is extended or adjusted under 35 U.S.C. 154(b) by 655 days.

(21) Appl. No.: 15/936,060

(22) Filed: Mar. 26, 2018

(65) Prior Publication Data
US 2019/0290105 A1  Sep. 26, 2019

(51) Int. Cl.
*A61B 1/00* (2006.01)
*A61M 25/06* (2006.01)

(52) U.S. Cl.
CPC .  *A61B 1/00135* (2013.01); *A61M 2025/0687* (2013.01); *A61M 2205/0216* (2013.01)

(58) Field of Classification Search
CPC ............ A61B 1/00135; A61B 1/00154; A61B 1/0125; A61B 1/018; A61B 1/00089
See application file for complete search history.

(56) References Cited

U.S. PATENT DOCUMENTS 4,531,943 A  7/1985  Tassel et al.
4,863,442 A  9/1989  Demello et al.
(Continued)

FOREIGN PATENT DOCUMENTS

CN  110353737 A  10/2019
DE  102019105632 A1  9/2019
(Continued)

OTHER PUBLICATIONS

"United Kingdom Application Serial No. 1904070.8, Office Action dated Feb. 1, 2022", 4 pgs.
(Continued)

*Primary Examiner* — Alexandra L Newton
(74) *Attorney, Agent, or Firm* — Schwegman Lundberg & Woessner, P.A.

(57) ABSTRACT

Disclosed embodiments include apparatuses, systems, and methods for providing an atraumatic sheath tip. Various disclosed embodiments seek to help reduce or avoid unnecessary tissue damage upon a sheath being extended to convey an elongated instrument for sampling or treatment. In an illustrative embodiment, an apparatus includes a deformable sheath tip configured to be positioned at a distal end of a sheath. The sheath defines therein a lumen configured to convey an elongated instrument. The sheath tip has a base end disposable at the distal end of the sheath and a contact end. The sheath tip has a first column strength along an axis of the sheath tip that is less than a second column strength of the sheath and a first degree of deformability that is greater than a second degree of deformability of the sheath.

21 Claims, 8 Drawing Sheets

(56) References Cited

U.S. PATENT DOCUMENTS

| | | | |
|---|---|---|---|
| 5,571,073 A | 11/1996 | Castillo | |
| 2004/0073089 A1* | 4/2004 | Nozue | A61B 1/00089 600/127 |
| 2004/0267092 A1* | 12/2004 | Ishibiki | A61B 1/00101 600/127 |
| 2008/0300460 A1* | 12/2008 | Sugita | A61B 1/00089 600/127 |
| 2011/0288392 A1 | 11/2011 | De La Rama et al. | |
| 2015/0105729 A1 | 4/2015 | Valeti et al. | |
| 2015/0174364 A1 | 6/2015 | Kennelly et al. | |
| 2016/0367233 A1* | 12/2016 | Mamiya | A61B 1/00 |
| 2017/0079519 A1 | 3/2017 | Sung et al. | |

FOREIGN PATENT DOCUMENTS

| | | |
|---|---|---|
| GB | 2144635 A | 3/1985 |
| GB | 2574295 A | 12/2019 |
| GB | 2574295 | 12/2022 |
| JP | 2003245244 | 9/2003 |
| JP | 2008054843 | 3/2008 |
| JP | 2008289761 | 12/2008 |
| WO | 2005056100 | 6/2005 |
| WO | WO-2006042157 A1 | 4/2006 |
| WO | 2014199519 | 12/2014 |
| WO | 2016021718 | 2/2016 |

OTHER PUBLICATIONS

"United Kingdom Application Serial No. 1904070.8, Office Action dated Sep. 25, 2019", 4 pgs.

"United Kingdom Application Serial No. 1904070.8, Office Action dated Oct. 6, 2021", 5 pgs.

"United Kingdom Application Serial No. 1904070.8, Response filed Dec. 6, 2021 to Office Action dated Oct. 6, 2021", 7 pgs.

"United Kingdom Application Serial No. 1904070.8, Subsequent Examination Report dated Feb. 1, 2022", 4 pgs.

"United Kingdom Application Serial No. 1904070.8, Response filed May 13, 2022 to Office Action dated Feb. 1, 2022", 8 pgs.

"United Kingdom Application Serial No. 1904070.8, Subsequent Examination Report under Section 18 (3) dated Jun. 15, 2022", 3 pgs.

"Japanese Application Serial No. 2019-56519, Notification of Reasons for Refusal dated Mar. 6, 2023", w English Translation, 11 pgs.

"Japanese Application Serial No. 2019-56519, Response filed Jun. 6, 2023 to Notification of Reasons for Refusal dated Mar. 6, 2023", w english claims, 9 pgs.

"United Kingdom Application Serial No. 1904070.8, Substantive Examination Report under Section 18 (3) dated Aug. 16, 2022", 4 pgs.

"United Kingdom Application Serial No. 1904070.8, Response filed Sep. 16, 2022 to Substantive Examination Report under Section 18 (3) dated Aug. 16, 2022", 6 pgs.

"Japanese Application Serial No. 2019-56519, Final Notification of Reasons for Refusal dated Oct. 2, 2023", w English Translation, 14 pgs.

\* cited by examiner

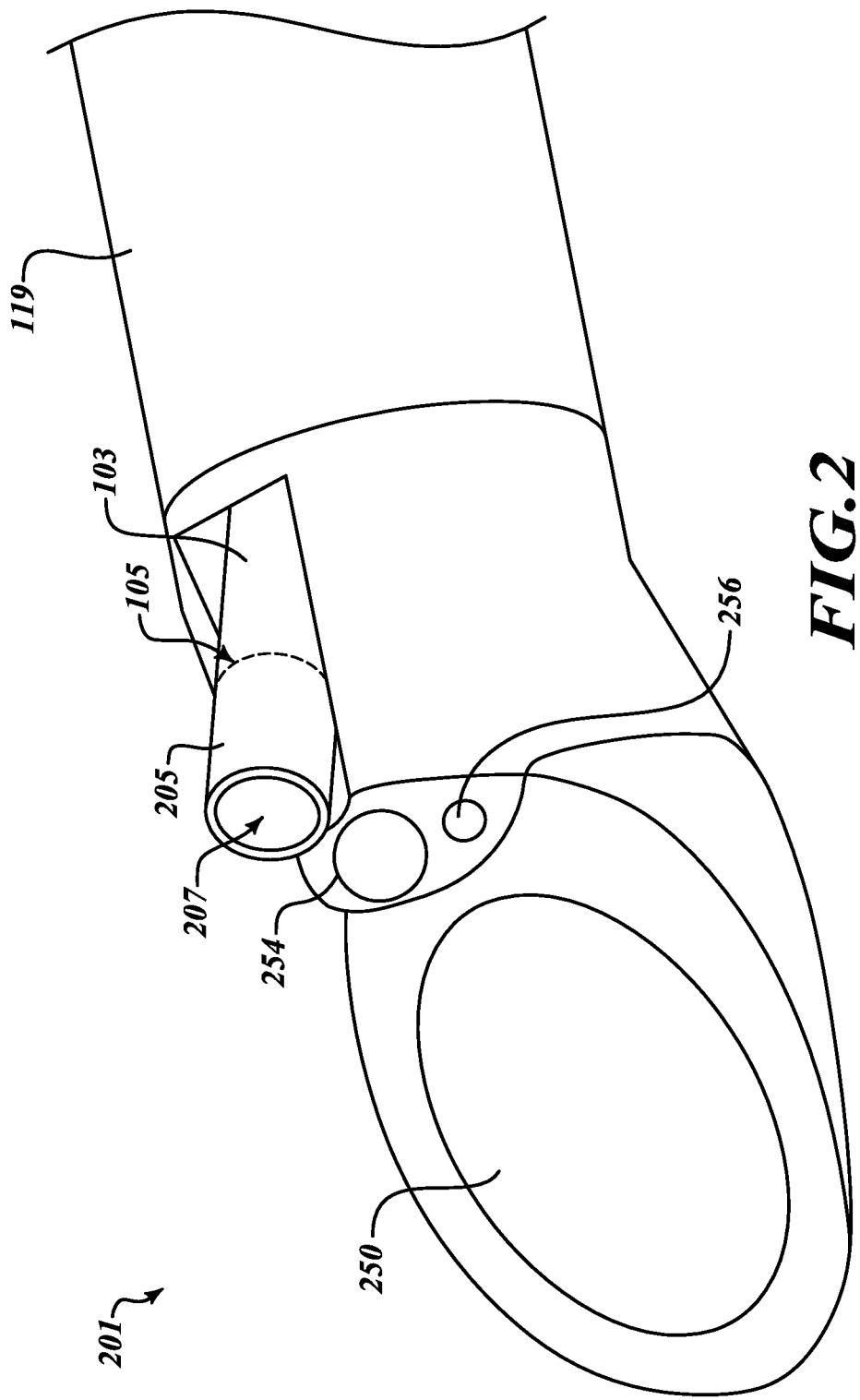

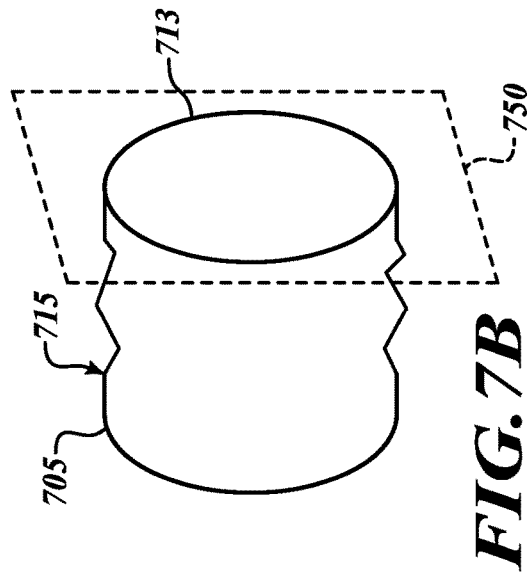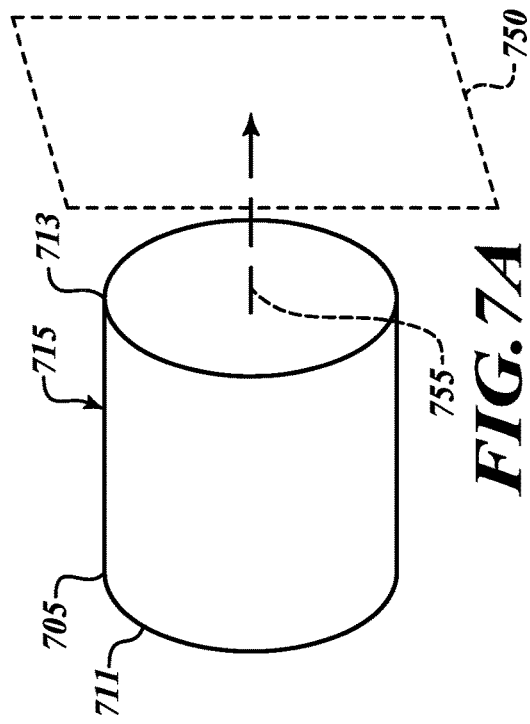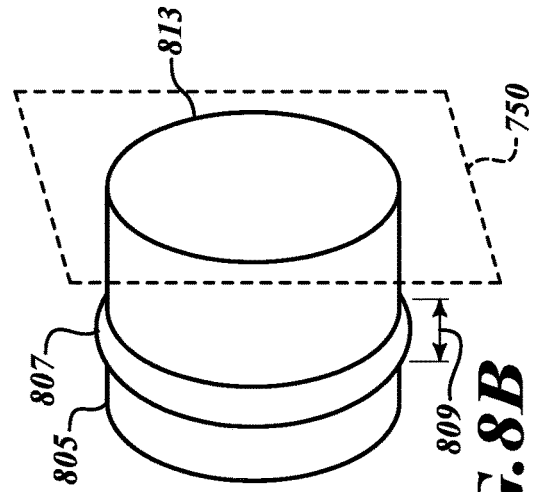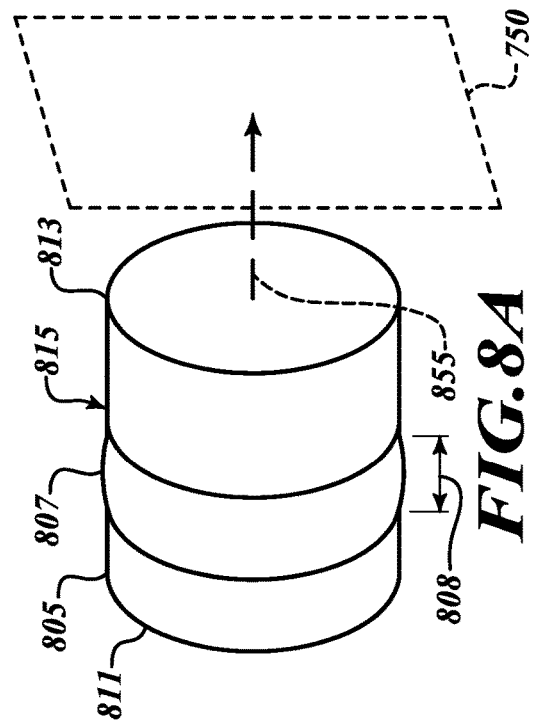

COMPLIANT, ATRAUMATIC SHEATH TIPS

FIELD

The present disclosure relates to a sheath used to extend an elongated instrument.

BACKGROUND

The statements in this section merely provide background information related to the present disclosure and may not constitute prior art.

The ability to access tissue within a patient's body without invasive surgery allows for ever-improving types of analysis, diagnosis, and treatment with reduced pain, reduced recovery time, and a reduced risk of complications. By way of two examples, endoscopic and catherization techniques have enabled evaluation and treatment of numerous internal lesions without invasive surgery.

For example, suspected or actual lesions may be sampled or treated by extending an elongated medical instrument, such as a sampling needle, through a sheath that is positioned by an insertion control system, such as a bronchoscope or an endoscope. The sheath may be extended from the insertion control system to position the elongated medical instrument, then the elongated instrument itself may be deployed for sampling or treatment.

Use of the insertion control system, while possibly avoiding invasive surgery, may pose its own challenges. For example, because the insertion control system may operate in tight spaces, it may be a challenge to engage in sampling or treatment at a desired position within in a body while minimizing or attempting to avoid trauma to the tissue at or near the desired position.

SUMMARY

Disclosed embodiments include apparatuses, systems, and methods for providing an atraumatic sheath tip. It will be appreciated that various disclosed embodiments seek to help reduce or avoid tissue damage upon a sheath being extended to convey an elongated instrument for sampling or treatment.

In an illustrative embodiment, an apparatus includes a deformable sheath tip configured to be positioned at a distal end of a sheath. The sheath defines therein a lumen configured to convey an elongated instrument. The sheath tip has a base end disposable at the distal end of the sheath and a contact end. The sheath tip has a first column strength along an axis of the sheath tip that is less than a second column strength of the sheath and a first degree of deformability that is greater than a second degree of deformability of the sheath.

In another illustrative embodiment, a system includes a sheath defining therein a lumen. An elongated medical instrument is configured to be delivered through the lumen in the sheath. An insertion control system is configured to convey the sheath to a desired location within a body. An instrument control system is configured to direct operation of the elongated medial instrument when the elongated medical instrument reaches a desired position. A sheath tip is configured to be positioned at a distal end of the sheath. The sheath tip has a base end disposable at the distal end of the sheath and a contact end. The sheath tip has a first column strength along an axis of the sheath tip that is less than a second column strength of the sheath. The sheath tip has a first degree of deformability that is greater than a second degree of deformability of the sheath.

In a further illustrative embodiment, a method includes preparing an elongated instrument for being conveyed into a body through a lumen in a sheath where the sheath is to be extended toward a tissue. The sheath includes a sheath tip configured to extend from a base end at a distal end of the sheath to a contact end, where the sheath tip is configured to be deformable with the sheath tip having a first column strength along an axis of the sheath tip that is less than a second column length of the body of the sheath. The sheath conveying the elongated instrument is inserted into the body, where the sheath tip deforms more readily than the body of the sheath upon a force being applied to the contact end as may result with contact with the tissue.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIG. 2 is a perspective view of a head on an insertion device including a sheath fitted with an illustrative sheath tip;

FIGS. 7A, 8A, 9A, and 10A are perspective views of illustrative sheath tips in an undeformed condition prior to contact with a surface;

FIGS. 7B, 8B, 9B, and 10B are perspective views of the sheath tips of FIGS. 7A, 8A, 9A, and 10A, respectively, in a deformed condition after contacting a surface;

FIGS. 11-14 are side views of additional illustrative sheath tips; and

Figure 15:
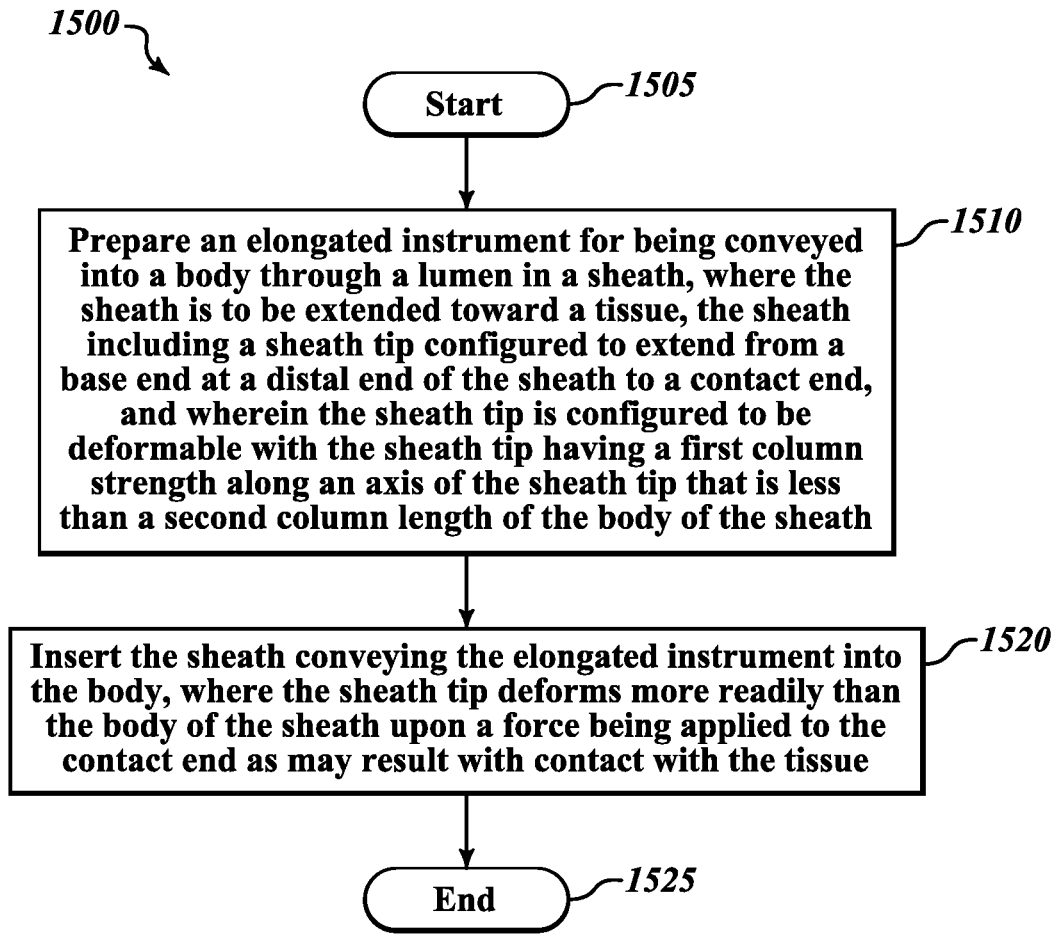

FIG. 15 is a flow diagram of an illustrative method of operating an apparatus equipped with a sheath tip.

DETAILED DESCRIPTION

The following description is merely illustrative in nature and is not intended to limit the present disclosure, application, or uses. It will be noted that the first digit of three-digit reference numbers and the first two digits of four-digit reference numbers correspond to the first digit of one-digit figure numbers and the first two-digits of the figure numbers, respectively, in which the element first appears.

The following description explains, by way of illustration only and not of limitation, various embodiments of sheath tips to help reduce or seek to prevent trauma upon extension of a sheath toward a surface, as well as systems including such sheath tips and methods of using the same. As will be described in detail below, in various embodiments the sheath tips are configured to deform upon contact with a surface to help reduce or seek to avoid causing trauma to tissue at or adjacent to a point where tissue is to be sampled or treated by an elongated instrument conveyed by the sheath.

It will be appreciated that various embodiments of sheath tips described herein have compositions and structures, including, in some embodiments, various openings formed in the sheath tips to reduce column strength of the sheath tips. The reduced column strength of the sheath tip enables the sheath tip to deform upon impacting a surface, thereby potentially helping avoid or lessen trauma to the surface.

Figure 1:
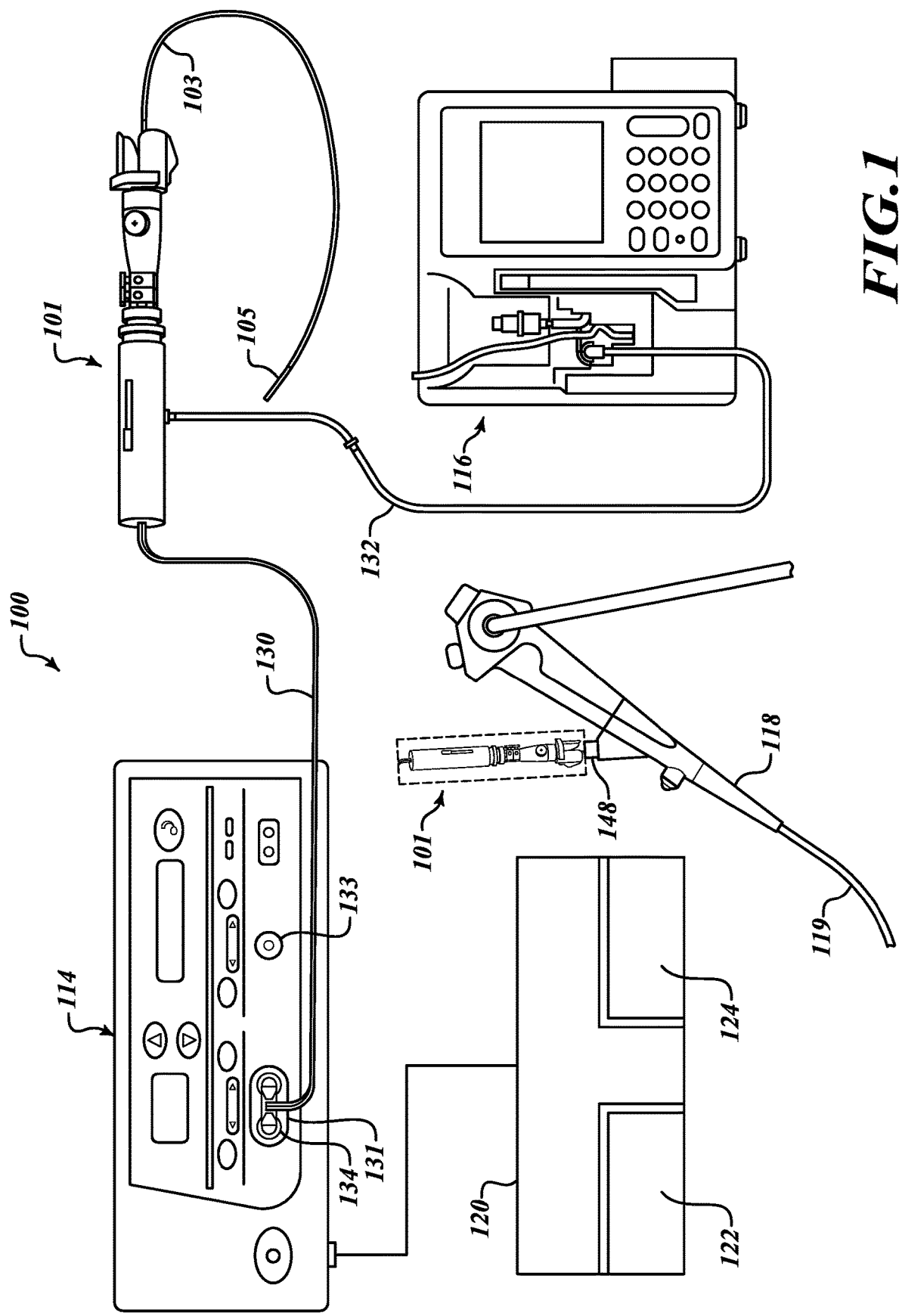
FIG. 1 is a block diagram in partial schematic form of an illustrative system for sampling or treating tissue using embodiments according to the present disclosure.

Referring to FIG. 1, in various embodiments, an illustrative system 100 is provided for sampling or treating tissue at a reference point in an anatomical region of a patient (not shown in FIG. 1). For one example, the system 100 may include a sampling device with a vacuum system for drawing a sample via a sampling needle. Alternatively, the system 100 may be a bipolar radio frequency (RF) system, as desired, for using electrical current to ablate or coagulate tissue in a patient. Further alternatively, the system 100 may include a mechanical or laser-based cutting system for incising tissue in a patient. Any such system may involve insertion of an elongated instrument into a patient to perform a desired procedure, and any such elongated instrument may be inserted into a patient via a sheath which may desirably end in a sheath tip as disclosed herein.

In some embodiments, the system 100 includes an elongated medical instrument controllable by a user interface 101, one or more instrument control systems 114 and 116, an insertion control system 118, and various supporting apparatuses. The user interface 101 may include a positioning device for positioning a distal end 105 of a sheath 103 relative to a position of interest in a body (not shown). The user interface 101 also may be configured to direct a position of an elongated instrument (not shown) that is housed within the sheath 103. The elongated instrument, for example, may include a sampling needle, as described below with reference to FIGS. 4-6, one or more electrodes, an imaging device, a probe, a cutting device, or any other elongated device. The one or more control systems 114 and 116 may be coupled to the elongated instrument and include devices to draw fluid or tissue, provide electrical current, provide fluid, monitor sensor data, or to perform other functions.

The insertion control system 118 may include a bronchoscope, an endoscope, or another insertion system configured to maneuver an insertion device 119 that may be equipped with a steering mechanism as well as optical, ultrasound, or other sensors to monitor the course of the insertion device 119. The user interface 101 may be received into the insertion control system 118 so that the insertion control system 118 at a port 148 for the insertion control system 118 so that the insertion control system 118 may direct the insertion device 119 to convey the distal end 105 of the sheath 103 to a desired location in a body where the user interface 101 then may be used to manipulate an associated elongated instrument to perform a desired function.

The system may represent any number of sampling or treatment systems. For one example, the system 100 may be a sampling system to collect a tissue sample using a sampling needle, such as described further below with reference to FIGS. 4-6. In such case, the insertion control system 118 may include a bronchoscope if the sample is to be collected from a respiratory system or an endoscope if the sample is to be collected from a digestive system. One instrument control system 114 may be used to receive and process sensor data and be operated by controls 120, 122, and 124. Another instrument control system 116 may be a pump or other vacuum source to draw a tissue or fluid sample from the sampling needle that may extend from the distal end 105 of the sheath 103.

For another example, the system 100 may be a cutting system for cutting through a tissue obstruction. In such case, the insertion control system 118 may include an endoscope to direct the if the sample is to be collected from a digestive system. One instrument control system 114 may be used to receive and process sensor data and be operated by controls 120, 122, and 124. Another instrument control system 116 may be a cutting control system to motivate a reciprocating and/or rotating cutting apparatus extending from the distal end 105 of the sheath 103.

For still another example, the system 100 may be an electrosurgical radio frequency (RF) system for ablating, cauterizing, or coagulating tissue. In such case, the insertion control system 118 may include a bronchoscope if the sample is to be collected from a respiratory system or an endoscope if the sample is to be collected from a digestive system. One instrument control system 114 may be a generator operating as a switchable power source 114 to apply electrical power to an elongated instrument extending from the distal end 105 of the sheath. The user interface 101 electrically communicates with the switchable power source 114 though an electrical conductor 130. In some embodiments, the electrical conductor 130 is connected to an outlet 131 when the system is operated in a bipolar mode. The electrical conductor 130 may be coupled with the outlet 131 using an electrical connector 134 configured to electrically engage the outlet 131. The switchable power source 114 can be operated with the use of a foot operated unit 120 electrically connected to the switchable power source 114. The foot operated unit 120 may include, for example, a pedal 122 that instructs the switchable power source 114 to apply electrical power to electrode(s) (described below) to cut and/or ablate tissue and a pedal 124 that instructs the generator 114 to apply a lower quantity of electrical power to the electrode(s) to coagulate tissue.

The user interface 101 is further connected to the conductive fluid source 116 with a tube 132 that facilitates the flow of liquid, for example saline solution or another conductive fluid, from the conductive fluid source 116 to the user interface 101. Another instrument control system 116 may be a conductive fluid source 116, such as an infusion pump controllable by a switch, to provide a conductive fluid to the distal end 105 of the sheath 103, where the conductive fluid may be vaporized by applied electrical power to generate heat to ablate or cauterize tissue.

The system 100 may include any number of medical systems or non-medical systems in which an elongated instrument is extended via a sheath 103 to perform an operation, and sheath tips in accordance with the present disclosure may be applied to the distal end 105 of the sheath 103 to facilitate such operations. Embodiments of the sheath tips of the present disclosure are not limited to use with any particular systems or functions. Any applications for use of the sheath tips of the present disclosure are provided solely for illustration and should not be taken as limiting.

Referring to FIG. 2, a head 201 of the insertion device 119 includes various sensor devices or related devices 250, 252, and 254 usable in positioning the distal end 105 of the sheath 103 (FIG. 1). For example, the head 201 may support an ultrasound transducer 250 that emits ultrasound energy and receives reflected ultrasound energy. The head 201 also may support a camera 254, for which a light source 246 may be provided to illuminate a region adjacent the head 201. The ultrasound transducer 250 and/or the camera 254 may be used to identify lesions or other regions of interest to be sampled or treated by an elongated instrument (not shown in FIG. 2) to be conveyed through the sheath 103.

The distal end 105 of the sheath 103 defines therein a lumen 207 from which the elongated instrument (not shown in FIG. 2) may extend. The distal end 105 of the sheath may be fitted with a sheath tip 205 as described below.

Figure 3A:
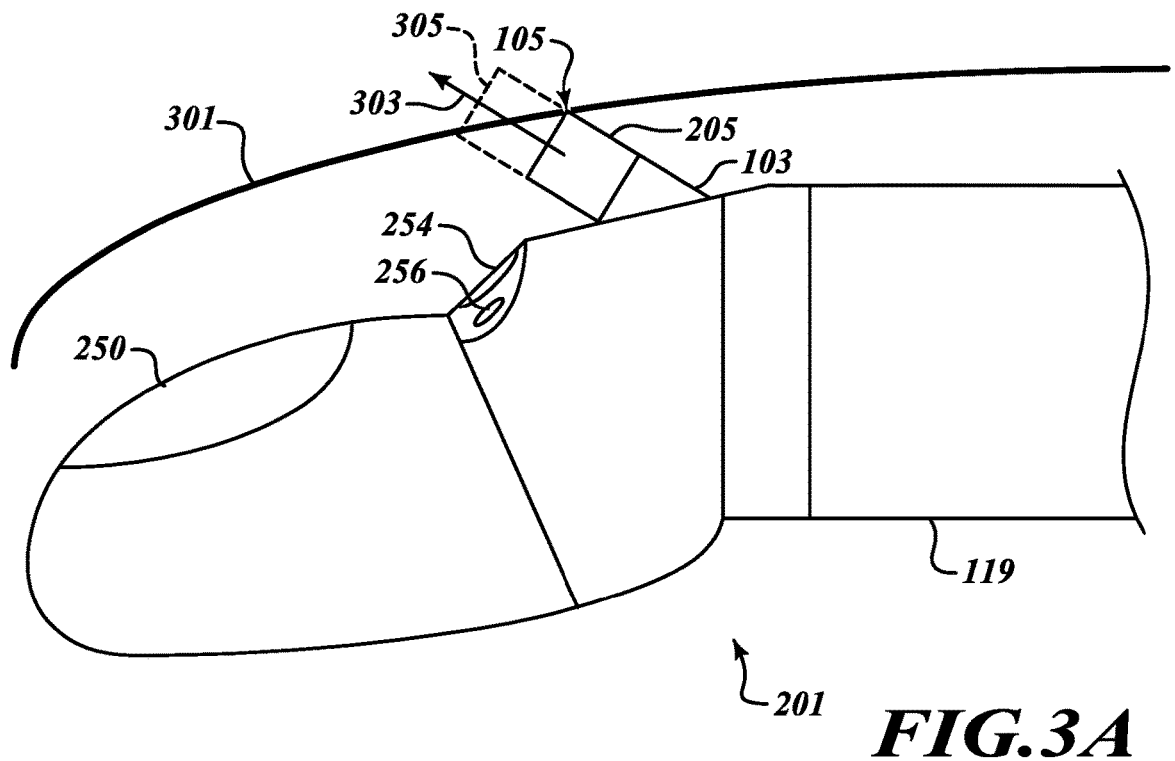
FIGS. 3A and 3B are side views of the head of the insertion device of FIG. 2 in preparation for extension of the sheath and following extension of the sheath, respectively, using an illustrative sheath tip.

Referring to FIG. 3A, the head 201 is disposed adjacent a tissue surface 301, such as an interior surface of a bodily tract into which the head 201 may be inserted. The head 201 is in position for extension of the sheath 103 before the sheath 103 is extended. When deployed, the sheath 103 will extend along an axis 303 that may potentially cause the sheath 103 to intersect the tissue wall. A projection 305 represented by a dashed line about the axis 303 shows how the sheath 103 may impinge upon the tissue surface 301. A sheath tip 205, disposed at the distal end 105 of the sheath 103, may help reduce or avoid trauma to the tissue surface 301 as described below with reference to FIG. 3B.

Figure 3B:
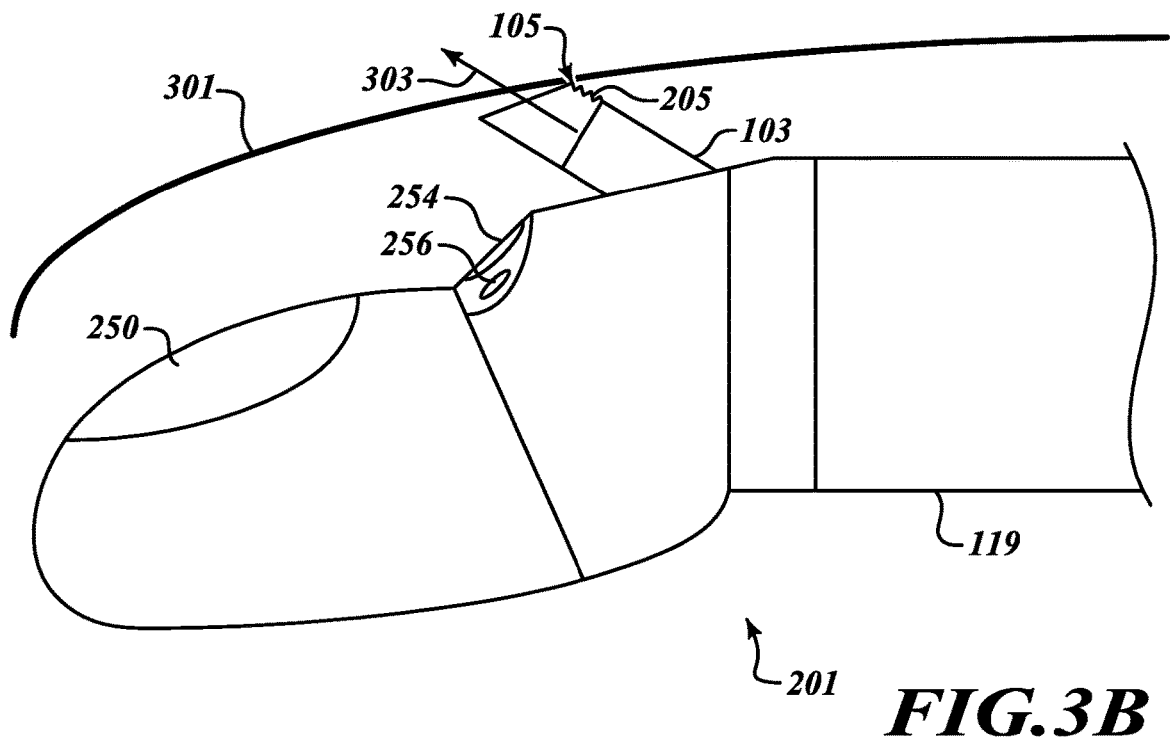

Referring to FIG. 3B, after extending the sheath 103, the sheath tip 205 has deformed upon contact with the tissue surface 301. Instead of the sheath 103 potentially deforming and potentially traumatizing the tissue surface 301 upon being extended along the axis 303 against the tissue surface 301, the sheath tip 205 at least partially crumples, collapses, or otherwise deforms to help potentially avert or minimize infliction of trauma upon the tissue surface 301.

Figure 4:
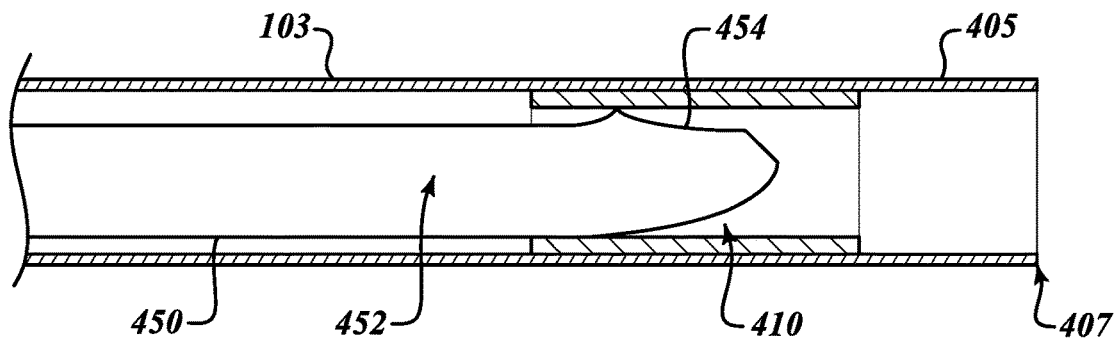
FIGS. 4-6 are cutaway views of an end of a sheath configured with illustrative sheath tips.
Figure 5:
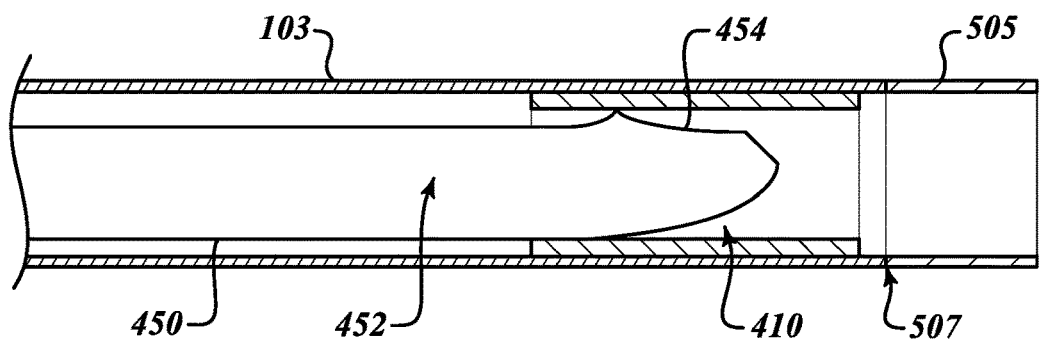
Figure 6:
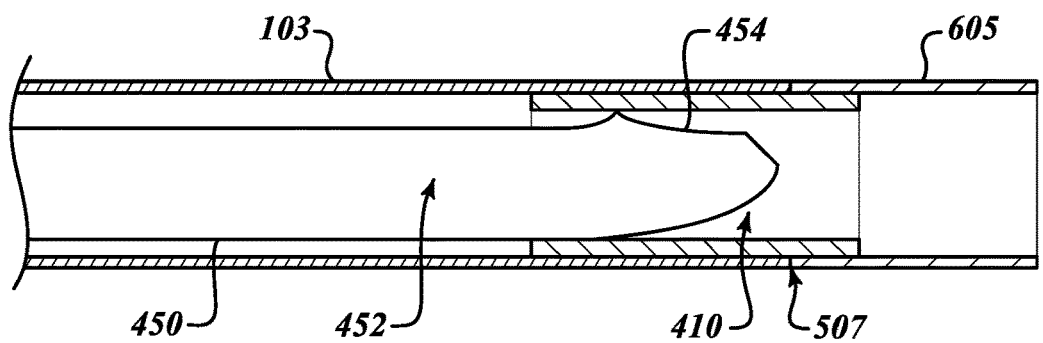

Referring to FIGS. 4-6, an elongated instrument 450 housed in the sheath 103 illustrates different configurations for inclusion of illustrative sheath tips 405, 505, or 605. The elongated instrument 450 used in FIGS. 4-6 is a sampling needle configured to draw a tissue sample from a tissue surface, lesion, or other body, and it includes an interior lumen 452 that terminates in an open sampling end 454. The elongated instrument 450 may be extended from the sheath 103 to collect a sample of tissue (not shown) at the open sampling end 454 that is then drawn through the lumen 452 by a vacuum source for collection and testing. As described in detail with reference to FIG. 1, however, it should be understood that the elongated instrument 450 may include any of a number of instruments including electrodes, cutting devices, other apparatuses, and the sampling needle is used here only by way of illustration and not limitation.

Referring to FIG. 4, a distal end 407 of the sheath 103 includes the sheath tip 405 that is integrally formed with the sheath 103. The sheath tip 405 may be molded, extruded, or otherwise formed as part of the sheath 103 when the sheath 103 is formed. The sheath tip 405 may include any number of the features described below with reference to FIGS. 7A-7B, 8A-8B, 9A-9B, 10A-10B, and 11-14 in order to provide the sheath tip 405 with a desired deformability to help avoid or reduce potential tissue trauma as described with reference to FIGS. 3A and 3B. Cuts or other modifications to the sheath tip 405 may be formed with mechanical or laser cutters or other devices after molding or extrusion of the sheath 103 and the sheath tip 405. The sheath 103 and the sheath tip 405 may be formed of plastic or any other flexible material.

Embodiments of the sheath 103 may be fitted with an insert 410 that is insertable or otherwise receivable within the sheath 103. The insert may serve the purpose of stiffening the sheath 103 short of the distal end 407 for purposes of assisting extension of the sheath 103 through the insertion device 119 and the head 201 (FIGS. 2 and 3A-3B). The insert 410 also may protect the sheath 103 from potential damage that may be caused by the elongated instrument 450, such as might be caused by a potentially sharp open sampling end 454 of a sampling needle while the sheath 103 and/or the insertion device 119 are maneuvered to a desired location within a body (not shown). The sheath tip 405 may be formed at a position beyond the end of the insert 410 or overlapping all or a portion of the insert 410, as further described below with reference to FIG. 6. With the presence of a relatively stiff insert 410 within the sheath 103, the deformability of the sheath tip 405 may be particularly beneficial in potentially helping to reduce or avoid tissue trauma upon deployment of the sheath 103.

Referring to FIG. 5, in other embodiments the sheath tip 505 is coupled with the sheath 103 at a distal end 507 of the sheath 103. In such embodiments, the sheath tip 505 may be molded, extruded, or otherwise separately from the sheath 103 when the sheath 103 is formed. The sheath tip 505 may be formed of plastic or any other suitable flexible material, and the sheath tip 505 may be joined to the distal end 507 of the sheath 103 by adhesives, heat welding, or any other technique that is operable to join together the materials that comprise the sheath 103 and the sheath tip 505. The sheath tip 505 may include any number of the features described below with reference to FIGS. 7A-7B, 8A-8B, 9A-9B, 10A-10B, and 11-14 in order to provide the sheath tip 605 with a desired deformability to help avoid or reduce potential tissue trauma as described with reference to FIGS. 3A and 3B. Cuts or other modifications to the sheath tip 505 may be formed with mechanical or laser cutters or other devices after molding or extrusion of the sheath tip 505. The cuts or modifications may be made before or after the sheath tip 505 is joined to the distal end 507 of the sheath 103.

Referring to FIG. 6, in other embodiments the sheath tip 605 is coupled with the sheath 103 at a distal end 607 of the sheath 103 where the distal end 607 of the sheath 103 overlaps with the insert 410. In such embodiments, the sheath tip 605 may be molded, extruded, or otherwise separately from the sheath 103 when the sheath 103 is formed. The sheath tip 605 may be formed of plastic or any other suitable flexible material, and the sheath tip 605 may be joined to the distal end 507 of the sheath 103 by adhesives, heat welding, or any other technique that is operable to join together the materials that comprise the sheath 103 and the sheath tip 605. The sheath tip 605 may be coupled with the insert 410 before or while the sheath tip 605 is joined with the sheath 103. Joining the sheath tip 605 with the distal end 607 of the sheath 103 at a point overlapping the insert may lend structural support to a joint where the sheath 103 and the sheath tip 605 are joined together. The sheath tip 605 may include any number of the features described below with reference to FIGS. 7A-7B, 8A-8B, 9A-9B, 10A-10B, and 11-14 in order to provide the sheath tip 605 with a desired deformability to help avoid or reduce potential tissue trauma as described with reference to FIGS. 3A and 3B. Cuts or other modifications to the sheath tip 605 may be formed with mechanical or laser cutters or other devices after molding or extrusion of the sheath tip 605. The cuts or modifications may be made before or after the sheath tip 605 is joined to the distal end 607 of the sheath 103.

FIGS. 7A-7B, 8A-8B, 9A-9B, 10A-10B, and 11-14 illustrate various embodiments of sheath tips configured to at least partially crumple, collapse, or otherwise deform to help reduce trauma or help avoid causing trauma to tissue impacted by the sheath tips upon extension of a sheath capped with the sheath tips are extended toward and against a tissue wall as described with reference to FIGS. 3A and 3B. In the embodiments of FIGS. 7A-7B, 8A-8B, 9A-9B, 10A-10B, and 11-14, each of the sheath tips is configured to have a column strength along an axis of the sheath tip that is less than a column strength of the sheath. As a result, each of the sheath tips has a degree of deformability that is greater than a degree of deformability of the sheath. The reduced column strength may result from at least a portion of the sheath tip having a different wall thickness than the sheath, from at least a portion of the sheath tip being made from a more deformable material than the sheath, or from the sheath having a configuration including cuts or folds at an end or along its length that renders the sheath tip more deformable, as described in the examples below.

With reference to FIGS. 7A-7B, 8A-8B, 9A-9B, and 10A-10B, it is noted that the surface 750 to which the sheath tips are directed and upon which they impinge is generally perpendicular to the axes of the sheath tips. However, it should be understood that surfaces on which the sheath tips may impinge and against which the sheath tips may desirably deform may be either perpendicular to the axes of the sheath tips, as shown in FIGS. 7A-7B, 8A-8B, 9A-9B, and 10A-10B, or at an angle to the axes of the sheath tips, as previously described with reference to FIGS. 3A and 3B.

Referring to FIG. 7A, a sheath tip 705 has a base end 711 that is configured to be integral, joined with, or otherwise disposed at a distal end of a sheath (not shown in FIG. 7A) as previously described with reference to FIGS. 3A-3B and 4-6. The sheath tip extends from the base end 711 along an axis 755 of the sheath tip 705 to a contact end 713. A body 715 of the sheath tip 705 may be formed of a different material having a rigidity that is less than that of the sheath. Alternatively or additionally, the sheath tip 705 may be of a same material as the sheath but with the sheath tip having a reduced thickness or thicknesses so as to be less rigid than the sheath. In either case, the sheath tip 705 is adapted to have reduced column strength or rigidity as compared with the sheath to provide a desired degree of deformability upon impact with a surface 750.

Referring to FIG. 7B, upon impinging upon the surface 750, the sheath tip 705 crumples or similarly deforms along the body 715 of the sheath tip 705 between the base end 711 and the contact end 715. The crumpling of the body 715 of the sheath tip 705 thus absorbs force resulting from impact of the sheath tip 705 and the surface 705. It should be appreciated that the deformation of the sheath tip 705 is generally uniform along the body 715 of the sheath tip 705. However, it should be understood that, if the sheath tip 705 were disposed at the end of the sheath so as to partially overlap with a sheath insert (not shown in FIGS. 7A and 7B), the portions of the sheath tip 705 overlapping the sheath insert 705 may not deform in the same way as the other portions of the body 715 of the sheath tip 705 between the contact end 713 and the overlapping portion of the body 715.

Referring to FIG. 8A, in other embodiments a sheath tip 805 includes a crumple zone 807 along a body 815 of the sheath tip 805 between a base end 811 and a contact end 813. In some embodiments, the crumple zone 807 has an undeformed length 808 having a reduced thickness and/or is comprised of a material having a reduced rigidity as compared to the sheath to provide a desired degree of deformability upon impact with a surface 750, such as a tissue surface.

Referring to FIG. 8B, upon impinging upon the surface 750, the crumple zone 807 at least partially collapses, as shown by the crumple zone 807 being deformed to a reduced length 809 to absorb some of the force resulting from the contact end 813 impacting against the surface 750. In some embodiments, the crumple zone 807 buckles outwardly (as shown in FIG. 8B) and/or inwardly around at least a portion of the circumference of the sheath tip 805.

Figure 9A:
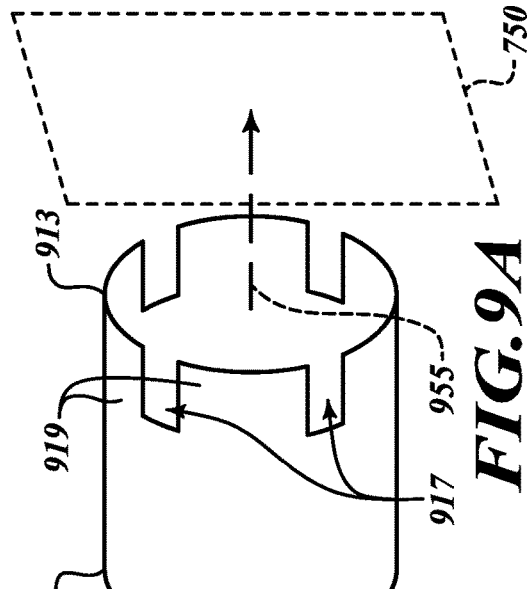

Referring to FIG. 9A, in other embodiments a sheath tip 905 includes longitudinal cuts 917 around a periphery of the contact end 913 of the sheath tip 905. The longitudinal cuts 917, which are generally parallel with an axis 955 of the sheath tip 905, result in a plurality of collapsible sections 919 around the periphery of the contact end 913 of the sheath tip 905.

Figure 9B:
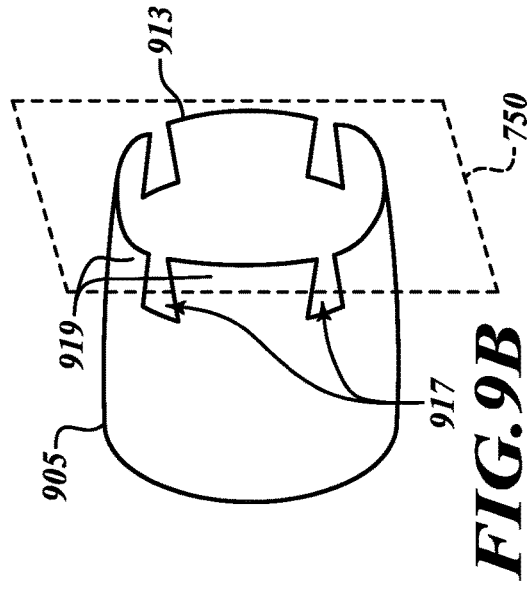

Referring to FIG. 9B, upon impinging upon the surface 750, the sections 919 collapse between and/or around the longitudinal cuts 917 to absorb some of the force resulting from the contact end 913 impacting against the surface 750. The sections 919 may buckle inwardly (as shown in FIG. 8B) and/or outwardly. In either case, it will be appreciated that the longitudinal cuts 917 reduce the column strength of the sheath tip 915, allowing for deformation of the sheath tip 905 against the surface 750.

Figure 10A:
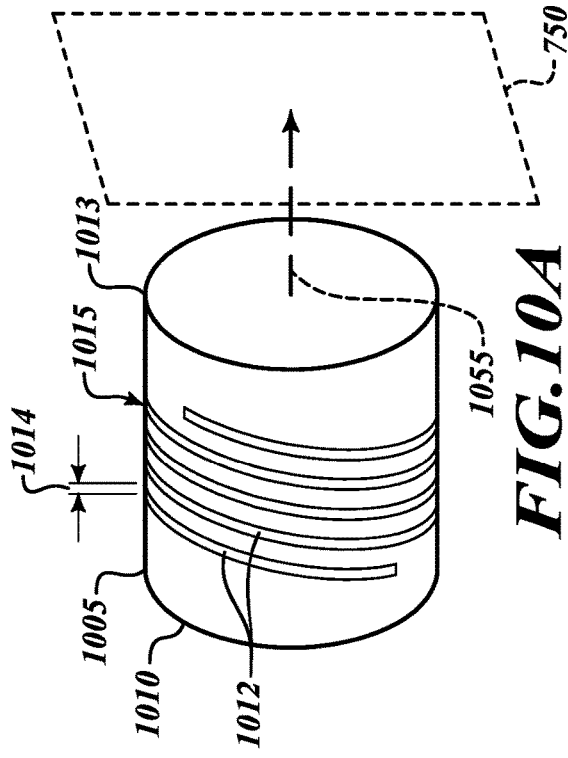

Referring to FIG. 10A, in other embodiments a sheath tip 1005 includes openings 1012 formed within a body 1015 of the sheath tip 1005 between the base end 1010 and the contact end 1013. The openings 1012 may be formed in the sheath tip 1005 during molding, or the openings 1012 may be cut into the sheath tip 1005 using mechanical or laser cutting devices. The openings 1012 may be oriented parallel with, perpendicular to, or, as shown in the embodiment of FIG. 10A, diagonal to an axis 1055 of the sheath tip. As shown in FIG. 10A, the openings 1012 are diagonal and extend fully around a circumference of the sheath tip one or more times in a corkscrew shape. The openings 1012 have an undeformed width 1014 relative to the axis 1015 that results in a reduction in the column strength of the sheath 1005.

Figure 10B:
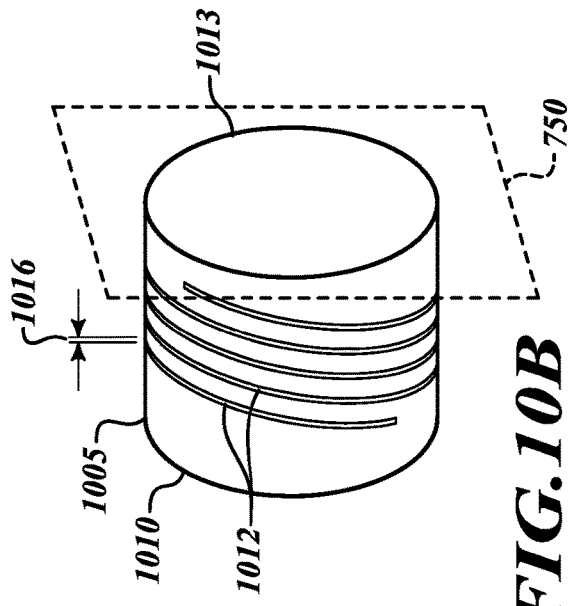

Referring to FIG. 10B, upon impinging upon the surface 750, the sheath tip 1005 deforms around the openings 1012, causing the openings 1012 to collapse to a deformed width 1016 to absorb some of the force resulting from the contact end 1013 impacting against the surface 750. Although not shown in FIG. 10B, the openings 1012 may also permit twisting or other deformation of the body 1015 of the sheath tip 1005 around the openings 1012 to permit further deformation of the sheath tip 1005 to avoid causing trauma to the surface 750.

Referring to FIGS. 11-14, cuts or openings in the sheath tip may be configured in a number of different shapes to provide a desired reduction in rigidity and/or an increase in deformability as compared to the sheath. The further examples of FIGS. 11-14 are provided solely for illustration and not by way of limitation.

Figure 11:
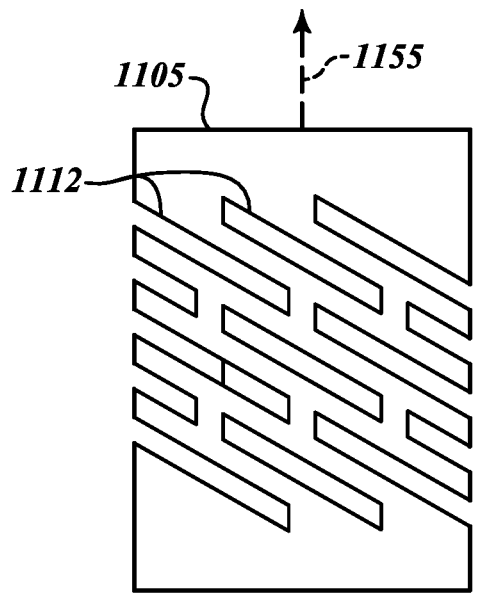
Figure 12:
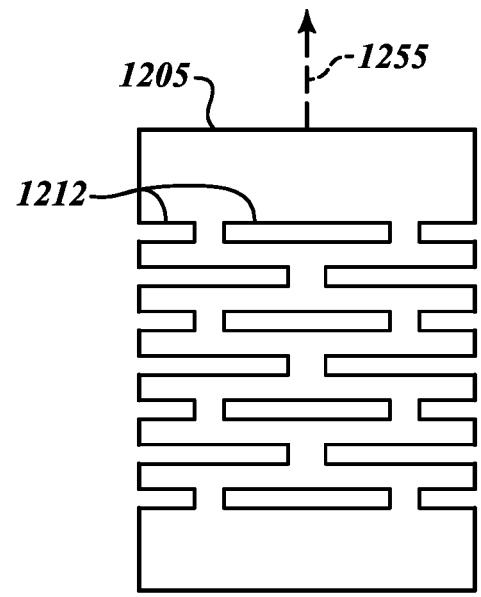

Referring to FIG. 11, a sheath tip 1105 may include openings 1112 that are diagonal relative to the axis 1155 of the sheath tip 1105. However, unlike the openings 1012 of the sheath tip 1005 of FIG. 10, the openings 1112 do not extend fully around a circumference of the sheath tip 1105. Referring to FIG. 12, a sheath tip 1205 may include openings 1212 that are perpendicular relative to the axis 1255 of the sheath tip 1205.

Figure 13:
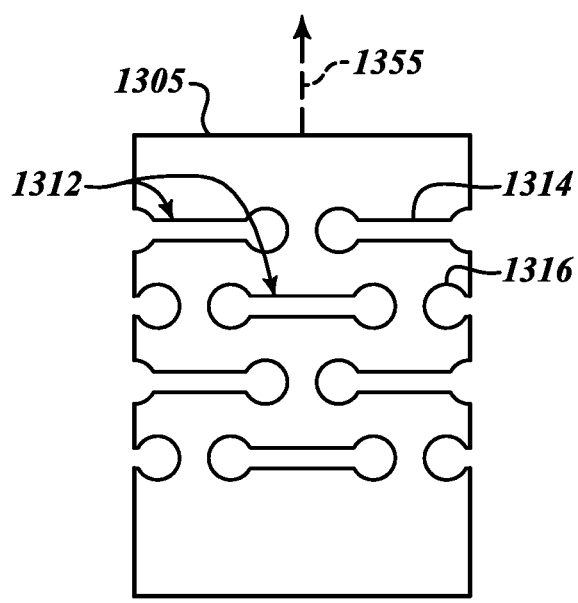

Referring to FIG. 13, openings or cuts in a sheath tip 1305 may include radial ends to help provide desired flexibility. The sheath tip 1305 includes openings 1312 that are generally perpendicular to an axis 1355 of the sheath tip 1305, as in the sheath tip 1205 of FIG. 12. However, each of the openings 1312 includes an elongated slot 1314 that terminates in radial end points 1316 that include, for example, a cylindrical opening or a conical opening formed around ends of the elongated slot 1314.

Figure 14:
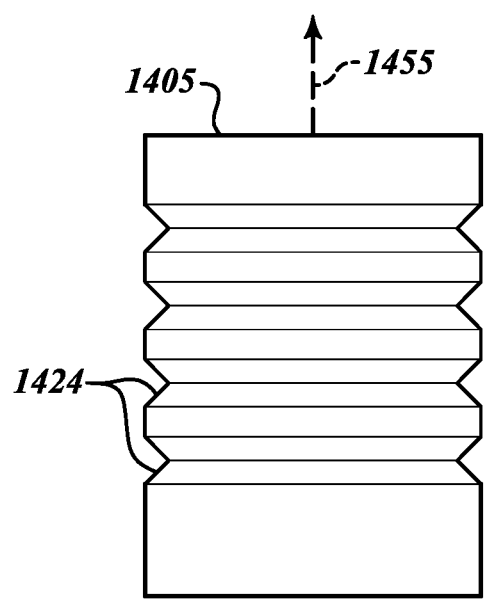

Referring to FIG. 14, instead of or in addition to openings extending through an entire thickness of a sheath tip, a sheath tip may be molded or partially cut away to form folds in the sheath tip to provide a desired degree of deformability. A sheath tip 1405 includes a plurality of folds or partial cuts 1424, in the nature of accordion-type folds, along an axis 1455 of the sheath tip 1405. The folds or partial cuts—which may be formed only on an outer surface of the sheath tip 1405, an inner surface of the sheath tip 1405, or on both the outer surface and the inner surface of the sheath tip 1405— may be formed in molding of the sheath tip 1405 or some material may be cut away from the sheath tip 1405 with mechanical or laser cutting devices to form the folds or partial cuts 1424. The varying thickness formed along the axis of the sheath tip 1405 reduces the column strength of the sheath tip 1405, resulting in a reduced rigidity/greater deformability to help reduce trauma that may be caused by the sheath tip 1405 impacting upon a surface.

It should be appreciated that a combination of structures explained here could be used to create a sheath tip having a desired degree of deformability. For example, diagonal openings (FIG. 11) could be formed with radial end points (FIG. 13). Openings formed along a body of a sheath tip (FIGS. 11-13) could be combined with folds or partial cuts (FIG. 14) along another portion of the body. Additionally, a sheath tip with folds or partial cuts or openings along the body could be combined with longitudinal cuts (FIGS. 9A-9B) at a contact end. Any of these structures could also be combined with a crumple zone (FIGS. 8A-8B). Similarly, using any of these structures can be combined with a sheath tip formed with a different material or a material having a different thickness than the sheath (FIGS. 7A-7B). Any such combinations may be used to provide a sheath tip having a desired degree of deformability. The aforementioned structures and/or combinations are provided by way of illustration and not by way of limitation in forming a sheath body having a desired degree of deformability.

Referring to FIG. 15 an illustrative method 1500 of using a sheath tip in deploying an elongated instrument via a sheath is provided. The method 1500 starts at a block 1505. At a block 1510, an elongated instrument is prepared for being conveyed into a body through a lumen in a sheath, where the sheath is to be extended toward a tissue. The sheath includes a sheath tip configured to extend from a base end at a distal end of the sheath to a contact end, where the sheath tip is configured to be deformable with the sheath tip having a first column strength along an axis of the sheath tip that is less than a second column length of the body of the sheath. The configuration of such sheath tips is described with reference to FIGS. 3A-3B, 4-6, 7A-7B, 8A-8B, 9A-9B, 10A-10B, and 11-14.

At a block 1520, the sheath conveying the elongated instrument is inserted into the body, where the sheath tip deforms more readily than the body of the sheath upon a force being applied to the contact end as may result with contact with the tissue. The insertion of the elongated instrument is described with reference to FIGS. 1-2 and 3A-3B; the deformation of the sheath tip is described with reference to FIGS. 3B, 4-6, 7A-7B, 8A-8B, 9A-9B, 10A-10B, and 11-14. The method 1500 ends at a block 1525.

It will be appreciated that the present descriptions of the sheath tips being used in the insertion of elongated instruments into a body via a sheath are not limiting to either the types of elongated instruments described or to use with medical instruments in a biological body. Sheath tips in the nature of those described could be used in any application where a lumen may contact a surface to which damage could result from impact of the lumen against the surface.

It will also be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:
1. An apparatus comprising:
an elongate imaging instrument including a head comprising an imaging sensor and an insertion device configured to deliver a sheath to a target tissue location within a patient, wherein the sheath is extendable out of the insertion device along an extension axis, and wherein the imaging sensor is positioned relative to the extension axis to enable imaging of a tissue sampling instrument delivered through the sheath;
a sheath tip forming a distal end of the sheath that defines therein a lumen configured to convey the tissue sampling instrument, the sheath tip having a cylindrical body extending between a base end and a contact end configured to contact a tissue surface, wherein the cylindrical body of the sheath tip includes a common outer diameter with the sheath and has a first column strength between the base end and the contact end along an axis of the sheath tip that is less than a second column strength of the sheath such that the cylindrical body of the sheath tip is configured to be deformable upon contact with the tissue surface between the contact end and the base end of the sheath tip.

2. The apparatus of claim 1, wherein the sheath tip is a separate structure configured to be attached to the distal end of the sheath.

3. The apparatus of claim 2, wherein the sheath tip is configured to be physically coupled to the distal end of the sheath at a sheath insert that is configured to be received within the lumen of the sheath.

4. The apparatus of claim 1, wherein the sheath tip is an integral section of the sheath.

5. The apparatus of claim 1, wherein the cylindrical body of the sheath tip has at least one characteristic chosen from a first thickness that is less than a second thickness of the sheath and a first rigidity that is less than a second rigidity of the sheath.

6. The apparatus of claim 1, wherein the cylindrical body of sheath tip has a varying thickness between the base end and the contact end wherein the varying thickness is less than a thickness of the sheath.

7. The apparatus of claim 1, wherein the cylindrical body of the sheath tip includes at least one crumple zone along around a circumference of the cylindrical body of the sheath tip a proximal distal away from the contact end, the crumple zone being buckleable responsive to application of a force to the contact end.

8. The apparatus of claim 1, wherein the cylindrical body of the sheath tip includes a plurality of circumferential cuts forming a plurality of accordion-shaped contours on an outside surface of the cylindrical body of the sheath tip, wherein the plurality of accordion-shaped contours is generally perpendicular to the axis of the sheath tip and configured to enable the cylindrical body of the sheath tip to deform along the plurality of accordion-shaped contours.

9. The apparatus of claim 1, wherein a distal edge of the contact end of the sheath tip defines a planar edge around the circumference of the distal edge.

10. The apparatus of claim 1, wherein the cylindrical body of the sheath tip is configured to be deformable between the contact end and the base end of the sheath tip without the contact end moving across the tissue surface.

11. A system comprising:
an elongate imaging instrument including a head comprising an imaging sensor and an insertion device;
a sheath defining therein a lumen, the sheath insertable into a patient's body through the insertion device and extendable out of the insertion device at the head;
an elongated medical instrument configured to be delivered through the lumen in the sheath;
an insertion control system configured to convey the sheath to a desired location within a body;
an instrument control system configured to direct operation of the elongated medial instrument when the elongated medical instrument reaches a desired position;
a sheath tip integrally formed with the sheath to form a distal end of the sheath with a common outer diameter, the sheath tip having a cylindrical body extending between a base end coupled to a reminder of the sheath and a contact end configured to contact a tissue surface upon extension out of the head, wherein the cylindrical body includes a crumple zone a proximal distance away from the contact end, the crumple zone is configured to be deformable upon the contact end contacting the tissue surface; and
a stiffening insert positioned within the sheath in a location proximal of a deformable portion of the sheath tip.

12. The system of claim 11, wherein the elongate imaging instrument includes a bronchoscope.

13. The system of claim 11, wherein the elongated medical instrument includes a sampling needle.

14. The system of claim 11, wherein the stiffening insert overlaps a distal end of the sheath and a proximal portion of the sheath tip.

15. An apparatus comprising:
a sheath defining a lumen that is dimensioned to convey an elongated tissue sampling instrument to a target tissue location;
an insertion device including a head comprising an imaging sensor and an exit port configured to deliver the sheath along an extension axis to the target tissue location within a patient; and
a sheath tip integrally formed with the sheath to form a distal end of the sheath, the sheath tip having a cylindrical body having a common outer diameter with the sheath, the cylindrical body extending between a base end at the distal end of the sheath and a contact end configured to contact a tissue surface upon extension of the sheath tip out of the exit port, wherein the cylindrical body of the sheath tip is configured to be deformable between the contact end and the base end of the sheath tip upon contact with the target tissue.

16. The apparatus of claim 15, wherein the sheath tip is an integral section of the sheath.

17. The apparatus of claim 15, wherein at least a portion of the cylindrical body of the sheath tip includes a first thickness that is less than a second thickness of the sheath.

18. The apparatus of claim 15, wherein the cylindrical body of the sheath tip includes at least one crumple zone along around a circumference of the cylindrical body of the sheath tip a proximal distal away from the contact end, the crumple zone being buckleable responsive to application of a force to the contact end.

19. The apparatus of claim 15, wherein the cylindrical body of the sheath tip includes a plurality of circumferential cuts forming a plurality of accordion-shaped contours on an outside surface of the cylindrical body of the sheath tip, wherein the plurality of accordion-shaped contours is generally perpendicular to the axis of the sheath tip and configured to enable the cylindrical body of the sheath tip to deform along the plurality of accordion-shaped contours.

20. The apparatus of claim 15, wherein a distal edge of the contact end of the sheath tip defines a planar edge around the circumference of the distal edge.

21. The apparatus of claim 15, wherein the cylindrical body of the sheath tip is configured to be deformable between the contact end and the base end of the sheath tip without the contact end moving across the tissue surface.

\* \* \* \* \*